United States Patent [19]

Müller et al.

[11] Patent Number: 4,703,646

[45] Date of Patent: Nov. 3, 1987

[54] OPERATING METHOD AND SENSOR FOR GAS ANALYSIS

[75] Inventors: Rudolf Müller, Söcking; Eckhard Lange, Gelting; Erich Schweizer, Munich, all of Fed. Rep. of Germany

[73] Assignee: Siemens Aktiengesellschaft, Berlin and Munich, Fed. Rep. of Germany

[21] Appl. No.: 867,965

[22] Filed: May 29, 1986

[30] Foreign Application Priority Data

May 30, 1985 [DE] Fed. Rep. of Germany ....... 3519410

[51] Int. Cl.⁴ ............................................. G01N 27/00
[52] U.S. Cl. .......................................... 73/23; 338/34
[58] Field of Search ..................... 73/23, 26, 27 R; 324/71.5; 357/2.5; 338/34; 422/98; 204/1 T (U.S. only), 1 Y, 1 S; 340/634

[56] References Cited

U.S. PATENT DOCUMENTS

| | | | |
|---|---|---|---|
| 3,865,550 | 2/1975 | Bott et al. | 73/23 |
| 3,999,122 | 12/1976 | Winstel et al. | 73/27 R |
| 4,020,830 | 5/1977 | Johnson et al. | 357/25 |
| 4,332,658 | 6/1982 | Tsuboshima | 204/425 |
| 4,423,407 | 12/1983 | Zuckerman | 338/34 |
| 4,457,161 | 7/1984 | Iwanaga et al. | 73/23 |
| 4,499,423 | 2/1985 | Matthiessen | 324/71.1 |
| 4,502,321 | 3/1985 | Zuckerman | 73/23 |
| 4,562,725 | 1/1986 | Oka et al. | 338/34 |

FOREIGN PATENT DOCUMENTS

DBP 1090002 3/1961 Fed. Rep. of Germany .
DE 3033730 3/1981 Fed. Rep. of Germany .
DE 3047782 7/1982 Fed. Rep. of Germany .

OTHER PUBLICATIONS

I. Lundstrom et al., "A hydrogen-sensitive MOS field--effect transistor", App. Phys. Let., vol. 26, (Jan. 15, 1975), pp. 55-57.

G. Zimmer et al., "A Fully Implanted NMOS, CMOS, Bipolar . . . ", IEEE Transactions on Elec. Dev., vol. ED-26, (Apr. 1979), pp. 390-395.

P. Bergveld, "Development, Operation, and Application of . . . ", IEEE Trans. on Biomedic. Engin., vol. BME-19, (Sep. 1972), pp. 342-351.

"Abstracts of Dissertations", IEEE Transactions on Biomedical Engineering, vol. BME-19, (Jan. 1972), pp. 68-71.

J. Katsuhara, "Physikalische Messung und Wahrnehmung von Duftstoffen", Umschau, vol. 20 (1970), p. 651.

J. O. Williams et al., "Halbleiter riechen", Umschau, vol. 11 (1969), p. 348.

"Figaro Gas Sensor TGS", Figaro Engineering Inc., Japan (Nov. 1, 1978).

Primary Examiner—Stewart J. Levy
Assistant Examiner—Hezron E. Williams
Attorney, Agent, or Firm—Hill, Van Santen, Steadman & Simpson

[57] ABSTRACT

A method for using a dynamic gas sensor for analysis and detection of one or more gases or gas components of a gas mixture includes using the response time constant for the gas sensor to the gas as a measured value so that detection ensues from the response time constant. Selectively different behavior and sensitivities of the gas sensor occurs by selection of its operating temperature, or by varying the temperature, or by modulation of its temperature at predetermined frequencies. A sensor for use in the present method may include a heating element integrated therewith and may also include a plurality of detectors arranged in an array.

26 Claims, 5 Drawing Figures

OPERATING METHOD AND SENSOR FOR GAS ANALYSIS

BACKGROUND OF THE INVENTION

1. Field of the Invention

The present invention relates to a method and sensor for gas analysis using a response time constant of the gas sensor.

2. Description of the Prior Art

A gas sensor with a semiconductor element having a selective means for detecting gases is disclosed in U.S. Pat. No. 3,999,122. The semiconductor element is a field effect transistor with a source, a drain, and a channel region extending between the source and drain and reaching to the surface of the semiconductor element. The selective means is a layer of β-carotene covering the channel region at the surface of the semiconductor element. The β-carotene is sensitive to gases and is used in the semiconductor field effect transistor to influence the charge in the channel region and thereby effect a different conductivity behavior of the field effect transistor, and/or to modify the threshold voltage.

Additional gas sensors are also disclosed in U.S. Pat. Nos. 4,020,830; 4,332,658; 4,499,423; and 4,457,161.

Gas sensors for detecting hydrogen present in a hydrogenous compound are known from Appl. Phys. Letters, Vol. 26 (1975), pp. 55–57. The gas sensors include an MOS transistor with a gate electrode of palladium. Palladium, like, for example, rhodium, is a metal that has a catalytic effect for hydrogen and is capable of splitting atomic hydrogen from molecular hydrogen compounds. The atomic hydrogen diffuses through the palladium metal of the gate electrode to the oxide layer of the MOS transistor disposed between the electrode and the semiconductor surface. There, the hydrogen is absorbed to effect the formation of a dipole layer that causes a change in the transistor threshold voltage.

The above-described gas sensor is not useful for gases that are free of hydrogen. In the publications "ESS-DERC", Munich, September 1979; "Int. Vac. Conf.", Cannes, September 1980; and "IEEE Transactions", Edition 26 (1979), pp. 390–396 are disclosed gas detectors for other gases, such as carbon monoxide. An MOS transistor with a gate electrode, preferably of palladium, having a plurality of holes therein that reach up to the metal oxide boundary layer, is shown. The use of an NMOS transistor is also considered in this context. Such transistors having a perforate palladium gate have good sensitivity for carbon monoxide and a greatly diminished "cross-sensitivity" for hydrogen. Such cross-sensitivity is sensitivity with respect to another gas in addition to the actual desired sensitivity of the sensor to a first gas. For such known sensors, the change of the threshold voltage is generally linearly dependent on the gas concentration. It is viewed as a disadvantage that the response of such gas sensors is a dynamic process that commences with a certain chronological delay in response to the influence of the gas, for example, carbon monoxide. In the aforementioned U.S. Pat. No. 4,499,423, electronic measures are employed to compensate for this disadvantageous time dependency. Both the delay time constant and the quantitative sensitivity of the known sensors are temperature dependent.

The cross-sensitivity of a sensor can be diminished by auxiliary measures. For example, the cross-sensitivity for hydrogen of the above-described carbon monoxide sensor can be reduced by more than an order of magnitude by applying a special protective layer.

While palladium has been used in gas sensors as described above, rhodium, platinum, and nickel are also known hydrogen-permeable substances. Silver, on the other hand, has a pronounced selective permeability for oxygen. Tin anhydride is used in a gas sensor, manufactured by the Figaro Company, which is sensitive to combustible and toxic gases. The sensitivity of the tin anhydride is based on a resistance change in the tin anhydride that has been rendered conductive.

Gas sensors that work on the principle of calorimetry are known by the name "Pellistor". A pellistor is composed of two platinum resistance wires into each of which a porous ceramic tablet is sintered. A catalyst is applied to one of the two ceramic tablets. A measurable increase in resistance is detectable at the platinum resistance wire having the ceramic table coated with the catalyst during catalytic burning of the gas to be detected. The increased resistance is sensed by inserting the two platinum resistance wires into a bridge circuit to compare the resistance of the first platinum wire to the second platinum wire.

Calorimetric effects in conjunction with catalysts are also known in the prior art. These include the combustion of hydrogen at a platinum catalyst, which produces NO from $NH_3$ with platinum or platinum-rhodium as a catalyst at 200°–250° C. Also produced is $NO_2$ from NO with a catalyst of $Al_2O_3$-$SiO_2$ gel at 100° C. upon the addition of a corresponding quantity of oxygen. $SO_2$ can be oxidized with oxygen to form $SO_3$ at elevated temperatures with the assistance of a platinum catalyst, and with the assistance of a catalyst of $Fe_2O_3$ and with $V_2O_5$ as a catalyst. With the assistance of palladium, CO can be oxidized to form $CO_2$ at temperatures of or above 150° C. With the assistance of a silver catalyst, methanol can be oxidized to form HCHO at 200°–400° C. Further catalytic processes are known from "Gmelins Handbuch der organischen Chemie", from Winnacker-Küchler, "Chemische Technologie", from Ullmans "Enzyklopädie der technischen Chemie" and from Reich, "Thermodynamik". Further publications that relate to semiconductor sensors are found in: IEEE Transactions on Biomedical Engineering, Vol. BME 19 (1972), pp. 342–351; IEEE Transactions on Biomedical Engineering, Vol. BME 19 (1972), pp. 70–71; Umschau (1970), p. 651; Umschau (1969), p. 348; German Pat. No. 1,090,002; and U.S. Pat. No. 3,865,550.

Zeolites are known as molecular sieves and are used for their selective effect on gases. Such molecular sieves have the property of allowing molecules of specific size values and below to pass therethrough and blocking the passage of larger molecules. Numerous examples of usable zeolites are known from Grubner et al., "Molekularsiebe", VEB Dt. Verl. d.Wissensch., Berlin (1968).

SUMMARY OF THE PRESENT INVENTION

An object of the present invention is to specify a sensor that is suitable for gas analysis, as well as to set forth an operating mode for a gas sensor so that individual gases and gas components of a gas mixture can be detected. In particular, the present sensor simultaneously selectively detects a plurality of individual gas components contained in a gas mixture, and determines or identifies the presence of unknown individual gases, in addition to other gases under given conditions. This, and other objects, are achieved with a sensor and an operating method using the time constant of the sensor response signal.

The instant invention is based, first, on the fact that gas sensors, such as gas sensors formed of MOS semiconductor elements having catalytically acting metals and/or a zeolite layer, have rising or trailing time constants of different values for various gases. The time constant is the duration until a prescribably defined fraction of the final value of the detector signal is reached, after the commencement or conclusion of the influence of a gas. Up to now, a time-delayed response of a gas sensor was considered a disadvantage, and gas detection was not carried out until a final value was reached.

It has been found that the value of the rising or declining time constant obtained with a given sensor for a specific gas, or concentration thereof, is dependent on the operating temperature of the detector during the measurement. It has also been found that different gases have different functions of temperature dependency which are characteristic for an individual gas given the same sensor.

An even more far-reaching finding is that changing operating temperatures and, in particular, modulated (periodically rising and falling fluctuations) operating temperatures of the sensor during the measurement provide a characteristic change or fluctuation of the detector signal for a gas or concentration thereof. It is possible to construct gas sensors or detectors such that the operating temperature thereof can be quickly changed or modulated over time, such as in the range of milliseconds to seconds. In contrast thereto, the measuring duration for identifying a measured value of a time constant can require longer time durations of seconds to minutes.

Thus, a further development within the scope of the present invention is that of modulating the operating temperature of a sensor, such as at a prescribed frequency, during the identification of the measured sensor signal, and thereby identifying the fluctuating measured signal derived from the value characteristic of a gas. A further finding is that there is also a dependency of the signal on the selected frequency of the modulation. Thus, a particular advantage lies in identifying the phase shift occurring between the fluctuating operating temperature of the sensor and the correspondingly modulated detector signal and, from the phase shift, generating a further signal to be interpreted. The inertia of the detector information with respect to the temperature changes is, thus, used.

A further information characteristic dependent on the modulation frequency of the sensor operating temperature is the derived amplitude of the detector signal for constant concentrations.

As a consequence of the above dependencies and function characteristics for a gas, the aforementioned possibilities are used to specify for a single sensor which of a plurality of gases, to which the sensor can respond is present at the moment of measurement. Also, a plurality of sensors having gas sensitivities differing from one another, as a consequence of their different structures, may have further sensitivity to various gases and gas concentrations by different variations of their respective operating temperatures.

The response, or rising, time constant can be identified and evaluated by commencing a relatively sudden influence of the gas or gas mixture at the time of measurement. Accordingly, an influence of the gas on the sensor that ends relatively suddenly is used for measuring a decaying, or falling, time constant. The term "relatively sudden" in the present sense means from milliseconds to several seconds relative to the measurement duration. A slow decay or slow decrease in the contact between the gas or gas mixture and the detector can result in an erroneous time constant measured from the detector signal.

After measuring the detector signal, a renewed decay while measuring the response time constant, or a renewed rise while measuring the decay time constant, plays less of a role in the control case. For example, it can be provided that the sensor is to be constantly exposed to the gas or gas mixture prior to measuring the decay time constant so that aging effects of the sensor can be considered. Correspondingly, measuring the rising time constant is preferred for chemically aggressive, or for toxic, gases, with the gas feed being ended as soon as possible.

In so far as gases, gas components, and gas mixtures are mentioned herein, vapors and the like are to be included among them. The term "gas" includes both pure gases and gas mixtures.

A plurality of mutually independent measured results can, thus, be achieved with the present invention by means of different operating temperatures for the sensor, the comparison of these measured results to one another supplying an evaluation signal indicating unequivocally the presence of a gas component. Insofar as the measurements and various operating temperatures of the detector, or sensor, are not carried out in chronological succession, a plurality of mutually independent measured values are achieved with the assistance of a plurality of individual detectors operated simultaneously which are at mutually different operating temperatures.

The same applies when using a detector having a zeolite layer, or a plurality of detectors having mutually different zeolite layers whereby the plurality of detectors are preferably disposed in an array. Individual detectors that are provided with identical and/or different zeolites, and that are also to be placed at operating temperatures that may differ from one another, can also be provided in a single array.

In accordance with the present invention, the gas to be sensed by the gas sensor flows in bursts controlled, for example, by solenoid valves, whose opening or closing times are adequately short in relationship to the time constants of the sensor. The time constants generally lie in the range of seconds through minutes so that an adequately brief duration opening or closing of the valves can be implemented.

For a semiconductor detector used as a dynamically functioning gas sensor, an advantage is realized by providing a heating resistance in integrated fashion with the sensor for setting an elevated operating temperature. Such a heating resistance is preferably arranged on the silicon chip in which the semiconductor detector element of the sensor is disposed.

It is especially advantageous for the temperature modulating frequency to be roughly equal to the reciprocal of the response time constant for the principle sensitivity of a specific gas or gas component. Different time constants derive for different gases or gas components for an individual detector. A principle sensitivity for a gas can, thus, be produced by selecting different modulating frequencies for the detector. A single individual detector can, thus, be made preferentially selective for various gases by selecting an appropriate modulation frequency.

In an embodiment of the present invention, an array formed by a plurality of individual detectors is provided, wherein the individual detectors are identically constructed. To distinguish a plurality of gas components from one another, especially simultaneously, using the array, individual detectors of the array are operated with mutually different modulation frequencies in accordance with a development of the present method.

In the previously identified U.S. Pat. No. 4,457,161, an array is disclosed composed of a plurality of individual detectors which are arranged in a matrix having i rows and j columns (i×j=n). Individual components of a gas mixture are distinguished from one another and are detected by the array. The evaluation is based on the mathematical solution of a linear equation system of n equations. Each individual equation represents the sensitivity spectrum of the sum of individual detectors of a row or column, or of each and every individual detector with respect to each of the individual components of the mixture, wherein an individual discrete sensitivity can also equal zero. Differing sensitivity spectrum for the individual detectors or detector rows and columns can be based on different temperatures.

For the sake of completeness, the thermic time constant of the individual detector must be shorter than the response time constant for a given gas component in order to achieve an effective temperature modulation.

The modulation of the temperature can be caused by either a heating or cooling element separately applied for this purpose, or by a modulation of the operating point and, thus, a modulation of the power loss. This is achieved by the impressed diode current, by modulation of the substrate voltage for an MOS transistor.

In this development, the advantages of a.c. measuring methods can be used to improve the signal-to-noise ratio by bandwidth limiting.

A detector of the present invention used according to the present method is preferably calibrated by series tests.

DETAILED DESCRIPTION OF THE PREFERRED EMBODIMENTS

Figure 1:
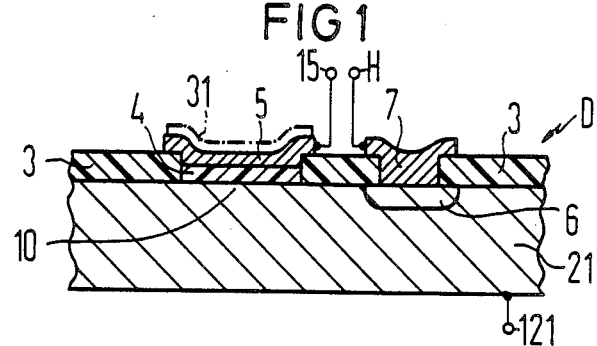
FIG. 1 is a lateral cross-section of an exemplary embodiment of a gas sensor according to the present invention.

FIG. 1 shows a sensor D having an MOS detector element 10 with an integrated heating resistance 6 for optionally setting a predetermined operating temperature of the detector 10. A protective layer 3 of silicon dioxide is disposed over a semiconductor substrate body 21, which is, for example, p-conductive silicon. A gate oxide layer 4 is preferably of thermally generated silicon dioxide. A metal layer 5 of, for example, palladium, forms a catalytically effective layer for interaction with a gas. An electrical terminal 15 is likewise provided.

The region 6 is formed by degeneratively n-doping the substrate body 21 as close as possible to the detector element 10 formed by the gate oxide layer 4 and the catalytic layer 5. An aluminum electrode 7 with an electrical connection terminal H is disposed on the surface of the substrate body 21 at one end of the region 6. The region 6, thus, forms a heating resistance. A second electrode can also be provided on the substrate body 21. A terminal 121 is provided on the substrate body 21 as well.

Figure 2:
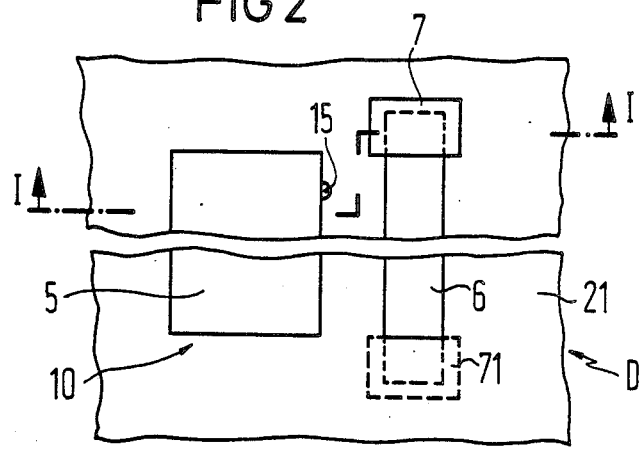
FIG. 2 is a plan view of the gas sensor shown in FIG. 1.

Referring to FIG. 2, the substrate body 21 of the sensor D includes a catalytically effective metal layer 5. An alternate embodiment for the heater resistance path of the region 6 is shown in dotted outline as including a second electrode 71. The region 6 can also be placed around the detector 10, such as around the catalytic layer 5, to encompass it as fully as possible so that the detector 10 can be heated to its prescribed operating temperature from more than one side.

Referring again to FIG. 1, a zeolite layer 31 is, in some forms of the sensor D, provided and is, for example, one of the known zeolites. For a detector 10 having a zeolite layer 31, the time constant which differs for various gases can, thus, be used for the detection of the various gases. Thus, different time constants arise not only for optionally prescribable, selected operating temperatures and/or modulation frequencies, but also as a result of the zeolite selected for the layer 31.

Figure 3:
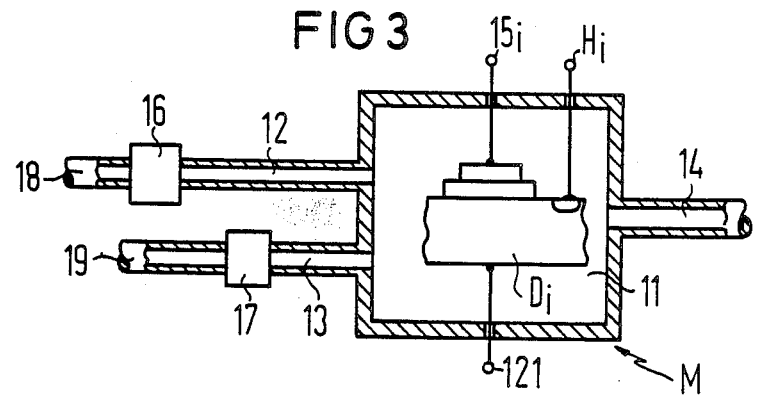
FIG. 3 is a diagrammatic representation of a measuring instrument according to the present invention, including a gas sensor as shown in FIG. 1.

In FIG. 3, an arrangement is shown that is particularly well suited for calibration, but which is also suitable for operation in accordance with the present invention. A sensor $D_i$ is shown disposed in an interior 11 of a measuring chamber M. The chamber interior 11 has two inlets 12 and 13, and an outlet 14. First and second solenoid valves 16 and 17 on the respective inlets 12 and 13 control the flow of gas bursts. A gas to be detected is supplied to the interior 11 through a conduit line 18 and a reference gas is provided through a conduit line 19. The sensor $D_i$ can be one of several sensors provided within the chamber M; in which case, the sensor $D_i$ is an individual $i^{th}$ detector element. The detector element $D_i$ has an individual electrical terminal $15_i$ and a shared terminal 121. A heating element for the detector element $D_i$ is connected to terminal $H_i$.

Figure 4:
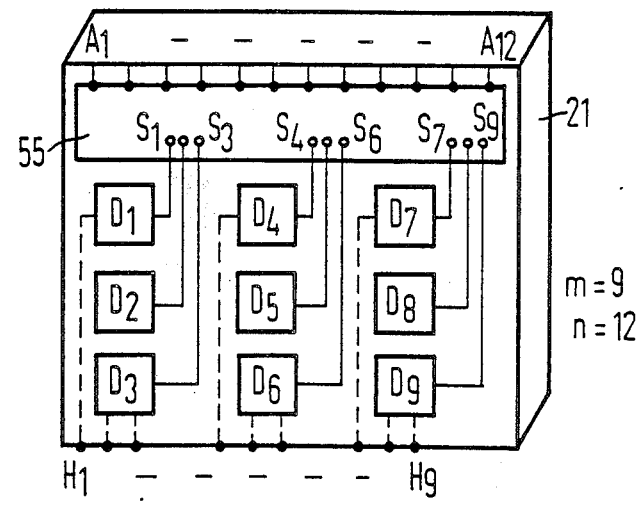
FIG. 4 is a diagrammatic perspective view of a detector array for use in the present invention.

A detector array is schematically illustrated in FIG. 4 and includes nine individual detectors $D_1$ through $D_9$, and an evaluation unit 55. The array is preferably in an integrated format on a substrate body 21, such as of semiconductor material.

The detectors $D_1$ through $D_9$ are individually brought to or held at mutually different temperatures. Alternately, one or more of the detectors $D_1$–$D_9$ are brought to or held at a temperature which deviates from that of the remaining detectors operating at room temperature. Current leads $H_1$ through $H_9$ are used to provide power to a heating element at each of the detectors $D_1$–$D_9$, which can be modulated to a correspondingly characteristic sensitivity as set forth above. Different characteristic sensitivities can be achieved by selecting different modulation frequencies. Output signals for the detectors $D_1$–$D_9$ are available at $S_1$–$S_9$.

Figure 5:
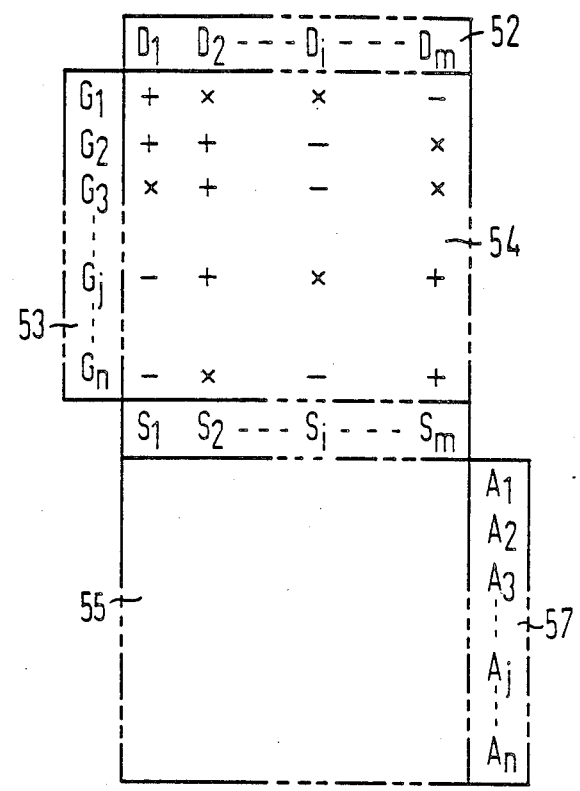
FIG. 5 is a matrix depicting the principle of pattern recognition as used in the present invention.

In FIG. 5, a diagram of a pattern recognition arrangement is shown with whose assistance an evaluation of output signals $S_1$ through $S_m$ established by the time constant values of individual sensors $D_1$ through $D_m$ is implemented. The evaluation of the output signals $S_1$–$S_m$ can be carried out simultaneously as well.

The schematic illustration of FIG. 4 shows the principle of a gas sensor having a detector array of individual detectors $D_1$, $D_2$, $D_3$... Individual ones of the detectors $D_1$, $D_2$, $D_3$... have sensitivities indicated in respective columns in a matrix 54 portion of the pattern recognition arrangement shown in FIG. 5. These sensitivities are indicated for individual gases or gas components $G_1$, $G_2$, $G_3$... $G_i$... $G_n$ of a gas mixture. A plus sign indicates a high sensitivity or principle sensitivity, whereas a St. Andrews cross, or x, denotes noticeably reduced sensitivities and a minus sign stands for insensitivity of the detector for the appertaining gas component $G_1$, $G_2$... The individual detectors form a row 52 and the gas components form a column 53 in the matrix 54. Such a matrix can also be formed of only two individual sensors $D_1$ and $D_2$.

A lower row corresponds to the signal outputs $15_i$ (for i=1, 2 ...) of the individual detectors $D_1$, $D_2$... which supply respective signals $S_1$, $S_2$... $S_m$. The signal $S_1$, for example, is the identified time constant of the individual detector $D_1$ to the gas components $G_1$, $G_2$–$G_n$. The signal $S_1$ also contains information that the individual detector $D_1$ is insensitive to the gas components $G_i$ and $G_n$. The remaining signals $S_2$ through $S_m$ yield corresponding time constant values. Insofar as the gas components $G_2$ and $G_n$ are not present, a signal $S'_1$ is obtained which differs from the signal $S_1$ in that the signal component otherwise based on the gas component $G_2$ for which the individual detector has a principle sensitivity is lacking in the signal $S'_1$. The lack of the gas $G_n$ supplies no contribution to the existing difference of $S'_1$ from $S_1$. The signal $S'_m$ appears given the lack of gas components $G_2$ and $G_n$ and differs from the signal $S_m$ in that the signal component of the principle sensitivity to the gas component $G_n$ and of the lower sensitivity to the gas $G_2$ is missing.

A pattern recognition matrix 55A is provided that operates in the fashion of a digital logic circuit, such as the evaluation unit 55. The matrix 55A is supplied with the detector signals which, for example, are the signals $S_1$ through $S_m$ actually occurring in response to a gas component mixture x. From the totality of supplied signals $S_1$ through $S_m$, the matrix 55A is in a position to draw conclusions regarding the presence or absence of individual gas components from a plurality n of gas components programmed into the pattern recognition matrix 55A. The plurality m of signals can thereby even be smaller than the plurality n by a corresponding relative number. The presence of a gas that has not been programmed into the matrix can at least be identified on the basis of an unassigned component in the measured time constant.

Mathematically expressed, the matrix 54 corresponds to the equation:

$$S_i = \sum_{j=i}^{j=n} (a_{ij} G_j)$$

with i from 1 through m for the signals $S_1$ through $S_m$. The aforementioned cross-sensitivities being denoted $a_{ij}$ with j different from i.

The goal in the prior art is to develop detectors that exhibit the smallest possible cross-sensitivities. For instance, the matrix elements $a_{ij}$ for i different from j are as small as possible in comparison to the matrix elements $a_{ij}$ with i equal to j. This requires at least one separate individual detector for every gas component (m≧n).

In the present invention, by contrast, the cross-sensitivities $a_{ij}$ with i different from j are used and evaluated to a degree essential to the invention. In the invention, cross-sensitivities are actually desired, contrary to the teachings of the prior art. The result of exploiting the cross-sensitivities is that the plurality m of individual detectors can be smaller than the plurality n of gas components to be detected.

When the $a_{ij}$ cross-sensitivity components are constant values of the sensitivity of the individual detector $S_i$, including a zero value, a linear equation system that is solved with the assistance of the pattern recognition matrix 55A derives. Insofar as the $a_{ij}$ component is a function dependent on the presence of the further gases G... present in addition to the gas components $G_j$, appropriate calibration places the pattern recognition matrix 55A in a position to also solve this equation system.

As such, calibrations of a detector array composed of individual detectors are undertaken using different known gas mixtures. The same is true when the sensitivities are a function of the existing concentration of the gas $G_j$ for j=i and/or of the gases $G_j$ present when j does not equal i. The pattern recognition matrix 55A is, thus, formed so that it may be used repeatedly for unequivocal identification and analysis of gases. For instance, the analysis is to be obtained in a known mathematical way with the assistance of the pattern recognition matrix 55A.

It is also possible to mathematically understand the present method of calibration and pattern recognition as a type of formation of correlation coefficients. For example, in the calibration procedure, the signals $S^*_{ij}$ for j from 1 through n are identified for every gas component $G_j$ prescribed for the purpose of calibration. These i·j values of $S^*_{ij}$ are stored in a memory of the pattern recognition matrix 55A. In the measurement of the gas mixture to be defined, the correlation coefficients $\beta_j$ are determined in accordance with the following rule:

$$S_j = \sum_{i=1}^{i=m} S_i S^*_{ij}$$

The correlation coefficient $\beta_j$ then indicates the part of the gas component $G_j$ to be defined.

The pattern recognition matrix 55A has a plurality of outputs $A_1$ through $A_n$ indicated in column 57 corresponding to the plurality n of gas components $G_1$ through $G_n$. Individual values for the gas components $G_1$–$G_n$ are thus available at outputs $A_1$–$A_{12}$ shown in FIG. 4.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a gas sensor to detect at least one gas, comprising the steps of:
   selectively switching between a first environment and a second environment influencing the gas sensor, said first environment including a gas to be tested and said second environment lacking the at least one gas to be detected, said selectively switching causing a response of the gas sensor that reaches a final value after a time interval upon the presence of the at least one gas to be detected;

measuring a dynamic response of the sensor for a measuring duration subsequent to said selectively switching;

identifying a time constant from said dynamic response, said time constant being characteristic of the at least one gas to be detected for the gas sensor; and evaluating the time constant to identify the at least one gas to be detected;

whereby said evaluation indicates at least whether the at least one gas to be detected is present in the gas to be tested.

2. A method as claimed in claim 1, wherein said step of selectively switching occurs in less time than said measuring duration.

3. A method as claimed in claim 1, wherein said step of selectively switching includes introducing said first environment in place of said second environment to cause a rising response of the gas sensor.

4. A method as claimed in claim 1, wherein said step of selectively switching includes introducing said second environment in place of said first environment to cause a falling response of the gas sensor.

5. A method as claimed in claim 1, further comprising:
    maintaining the gas sensor at an operating temperature different from ambient temperature at least during the measuring duration.

6. A method as claimed in claim 1, wherein the measuring duration is at least as long as the time constant of the dynamic response.

7. A method as claimed in claim 1, wherein a thermal time constant of the gas sensor is shorter than the measuring duration.

8. A method as claimed in claim 7, further comprising:
    changing the temperature of the gas sensor from a first prescribed temperature to a second prescribed temperature during the measuring duration.

9. A method as claimed in claim 7, further comprising:
    modulating the temperature of the gas sensor during the measuring duration.

10. A method as claimed in claim 9, wherein said temperature modulation is at a predetermined modulation frequency.

11. A method as claimed in claim 10, wherein said modulation of the sensor temperature occurs with a frequency that is the reciprocal of the time constant for the gas to be detected.

12. A method as claimed in claim 9, wherein said step of modulating the gas sensor temperature produces a modulated gas sensor response, and wherein said step of evaluating the time constant includes:
    evaluating a phase shift between the modulated sensor temperature and the response of the gas sensor.

13. A method as claimed in claim 9, wherein said step of evaluating the time constant includes:
    evaluating the amplitude of the gas sensor response during the sensor temperature modulation.

14. A method as claimed in claim 1, wherein the gas sensor is provided with a catalytically acting layer.

15. A method as claimed in claim 1, wherein the gas sensor is provided with a zeolite layer.

16. A method as claimed in claim 1, wherein the gas sensor has a plurality of detector elements with different time constants,
    wherein said step of measuring includes:
        measuring a dynamic response for each of said plurality of detector elements, and
    wherein said step of identifying includes:
        identifying a time constant for each of said plurality of detector elements.

17. A method as claimed in claim 16, wherein said plurality of detector elements are combined in an array, and further comprising the steps of:
    applying the sensor responses of said plurality of detector elements to a matrix; and
    identifying the gas to be tested using the principle of pattern recognition.

18. A method as claimed in claim 16, wherein each of said plurality of detector elements has the same zeolite layer.

19. A method as claimed in claim 16, wherein each of said plurality of detector elements has a different zeolite layer.

20. A method as claimed in claim 16, wherein a greater number of gases are detectable by the gas sensor than the number of said plurality of detector elements.

21. A method as claimed in claim 1, wherein the gas sensor includes a plurality of gas detectors, and further comprising the step of:
    modulating the temperature of each of said plurality of gas detectors with a different frequency; and
    identifying a time constant for each of said plurality of gas detectors.

22. A method as claimed in claim 1, wherein the gas sensor includes a plurality of gas detectors, and further comprising the steps of:
    operating each of said plurality of gas detectors at a different temperature; and
    identifying a time constant for each of said plurality of gas detectors.

23. A method for detecting at least one gas using a gas sensor having: a semiconductor substrate body; an oxide gate layer provided on said semiconductor body; a catalytically effective layer for interaction with at least one gas provided over said gate layer to form a gas detector, said catalytically effective layer being a gate electrode; a first electrical connection connected to said catalytically effective layer; a second electrical connection connected to said semiconductor substrate body; and a heating resistance provided on said semiconductor substrate body adjacent said catalytically effective layer, said heating resistance including a heating electrode and a heating terminal connected to said heating electrode; a silicon dioxide protective layer over portions of said semiconductor substrate body; comprising the steps of:
    changing between a first gas influencing said gas sensor and a second gas influencing said gas sensor to cause a change in the response signal of said gas sensor when the at least one gas to be detected is in one of the first gas and the second gas;
    changing the temperature of the gas sensor during a measuring duration to effect a change in the sensor response to the gas to be detected;

identifying a time constant of the gas sensor from the change in the sensor response signal occurring during the measuring duration; and evaluating the time constant to determine whether the gas to be detected is present in one of the first gas and the second gas.

24. A method as claimed in claim 23, wherein a zeolite layer is provided over said catalytically effective layer.

25. A method as claimed in claim 23, wherein said heating resistance is formed substantially around said catalytically effective layer to heat said gas sensor evenly.

26. A method as claimed in claim 23, wherein said gas sensor includes an array of a plurality of integrated gas detectors and heating resistances having selectively different time constants for the gas to be detected, and further comprising:

identifying a time constant for each of said plurality of integrated gas detectors and heating resistances; whereby a greater number of gases are detectable by said gas sensor than the number of detectors in said array.

* * * * *